United States Patent [19]

Jacobson

[11] Patent Number: 4,483,994
[45] Date of Patent: Nov. 20, 1984

[54] PROCESS FOR THE PRODUCTION OF ALKYLENE CARBONATES AND OXIDES

[75] Inventor: Stephen E. Jacobson, Morristown, N.J.

[73] Assignee: The Halcon SD Group, Inc., New York, N.Y.

[21] Appl. No.: 468,428

[22] Filed: Feb. 22, 1983

[51] Int. Cl.³ .................. C07D 317/36; C07D 317/38
[52] U.S. Cl. .................................... 549/230; 549/229; 549/549; 549/524; 549/518
[58] Field of Search ...................... 549/230, 524, 229

[56] References Cited

U.S. PATENT DOCUMENTS

| | | | |
|---|---|---|---|
| 1,907,891 | 5/1933 | Steimmig et al. | 549/230 |
| 2,667,497 | 1/1954 | Cline | 549/230 |
| 2,773,881 | 12/1956 | Dunn | 549/230 |
| 2,784,201 | 3/1957 | Chitwood | 549/230 |
| 3,025,305 | 3/1962 | Verdol | 549/230 |
| 3,641,067 | 2/1972 | Kruse | 549/524 |
| 3,923,842 | 12/1975 | Wu | 549/230 |
| 4,009,183 | 2/1977 | Fumagalli et al. | 549/230 |
| 4,021,453 | 5/1977 | Brill | 549/524 |
| 4,146,545 | 3/1979 | Leonard | 549/524 |
| 4,192,814 | 3/1980 | Johnson | 423/111 |
| 4,224,223 | 9/1980 | Wheaton et al. | 549/230 |
| 4,226,778 | 10/1980 | Venturello et al. | 549/230 |
| 4,231,937 | 11/1980 | Kao et al. | 549/230 |
| 4,233,221 | 11/1980 | Raines et al. | 549/230 |
| 4,247,465 | 1/1981 | Kao et al. | 549/230 |
| 4,325,874 | 4/1982 | Jacobson | 549/230 |

OTHER PUBLICATIONS

W. Kruse et al., J. Org. Chem., vol. 36 (1971), No. 8, pp. 1154–1155.
S. Szokacs et al., Magy. Kem. Foly, 89(9), 413 (1981), (English translation).

Primary Examiner—Norma S. Milestone
Attorney, Agent, or Firm—William C. Long; Riggs T. Stewart; Daniel R. Zirker

[57] ABSTRACT

A process for the production of alkylene carbonates, such as propylene carbonate, is disclosed. The process involves reacting the desired olefin with a thallic oxide or a weak acid thallic salt with carbon dioxide in an aqueous, organic solvent containing, halogen-free system.

12 Claims, No Drawings

PROCESS FOR THE PRODUCTION OF ALKYLENE CARBONATES AND OXIDES

BACKGROUND OF INVENTION

1. Field of Invention

This invention is related to a process for the production of alkylene carbonates and oxides, and particularly to the production of propylene carbonate through a process comprising reacting propylene with a thallic salt of a carboxylic acid or thallic oxide and a carboxylic acid and carbon dioxide in an aqueous, organic solvent medium.

The olefin, e.g. (alkylene) carbonate products obtained through the process of this invention are useful commercial articles, particularly as reactants for the preparation of alkylene oxides such as propylene oxide through the decomposition of the carbonate and as organic polymer fiber forming resin solvents.

2. Description of Prior Art

W. Kruse, et al, *J. Org. Chem.* 30th Vol. pp.114 (71), describes the preparation of certain selected epoxides through the oxidation of the corresponding olefin with thallic acetate in weakly solvating media. No carbon dioxide is present in the Kruse system.

The Prior Art discloses several methods for the production and use of aklylene carbonates, and particularly ethylene and propylene carbonates. Alkylene carbonates have been made by at least three different approaches to date. One such technique is by the reaction of the corresponding alkylene oxide with carbon dioxide. Examples of this reaction can be seen in U.S. Pat. Nos. 2,667,497, 2,773,881 and 4,233,221. Naito et al., *Chem. Soc. of Japan* (82) No. 2 pp.290 discloses the free anionic additions of oxirane and its alkyl, aryl and halomethyl derivatives with carbon dioxide catalyzed by potassium carboxylates or carbonates through the addition of the crown ether, resulting in the formation of five membered cyclic carbonates.

Another technique is through the reaction of carbon dioxide with selected halohydrins. In U.S. Pat. No. 1,907,891 alkali carbonates are reacted with vicinal glycol chlorohydrins to produce the corresponding alkylene carbonates. In U.S. Pat. No. 2,784,201, the chlorohydrin is reacted with an alkali metal lower alkyl carbonate. In U.S. Pat. No. 3,923,842, as part of a three-step process to produce an alkylene oxide, the second step involves the reaction of a halohydrin with carbon dioxide to form an alkylene carbonate. Similar reactions are also revealed in U.S. Pat. Nos. 4,226,778 and 4,231,937.

Still another approach involves the direct reaction of olefins with carbon dioxide to produce alkylene carbonates. In U.S. Pat. No. 3,205,305 this reaction is carried out in the presence of two catalysts; the first a heavy metal oxide compound and the second a halide or hydroxy form of an ammonium compound. In U.S. Pat. No. 4,009,183 the reaction is carried out in the presence of an elemental iodine or iodide compound and a manganese compound. In U.S. Pat. No. 4,325,874 a process for the preparation of alkylene carbonates through the reaction of the corresponding olefins with carbon dioxide in the presence of iodine or an iodide compound and an oxide or a weak acid salt of thallium(III) is disclosed. U.S. Pat. No. 4,247,465 discloses the preparation of a cyclic alkylene carbonate ester from the reaction of an olefin with carbon dioxide and oxygen in the presence of an iodine-iron catalyst.

Oxidation of thallous compounds to their thallic forms have been disclosed in various publications. A number of these are discussed in U.S. Pat. No. 4,192,814.

All of these reactions, however, have the drawback of involving at least one of the following impediments; very high working temperatures and pressures, the use of toxic reagents such as phosgene, which give rise to the collateral formation of undesired by-products such as glycols which are difficult to separate, or, the use of corrosive reagents such as iodine which can gradually destroy reaction equipment and other containers. In particular, no reaction to date has been able to directly prepare alkylene carbonates from the corresponding olefins without the use of corrosive halides or some other serious process flaw.

OBJECTS OF THE INVENTION

Accordingly, it is an object of this invention to provide a method for synthesizing alkylene carbonates and oxides which is substantially more effective than prior art methods having excellent yields obtained in a process operating under mild temperatures and pressures.

It is another object of this invention to provide an improved method for the direct synthesis of alkylene carbonates from the olefin which eliminates the use of corrosive halogen compounds and insoluble catalysts.

SUMMARY OF INVENTION

This invention involves a process for the preparation of olefin, (alkylene) carbonates and oxides, and particularly propylene carbonate, in a halogen-free reaction zone, comprising reacting the corresponding olefins with a thallic oxide and a weak acid, or, a weak acid thallic salt, e.g., thallic acetate, and a stoichiometric excess of carbon dioxide in an aqueous, organic solvent, e.g., sulfolane, reaction medium. The reaction apparently proceeds according to the following stoichiometric equation, using propylene, thallic acetate, water and carbon dioxide as reactants:

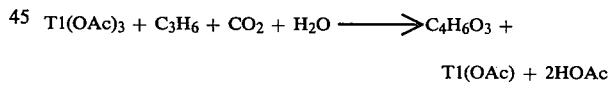

$$Tl(OAc)_3 + C_3H_6 + CO_2 + H_2O \longrightarrow C_4H_6O_3 + Tl(OAc) + 2HOAc$$

Upon completion, the formed reaction products, particularly the alkylene carbonate and oxide, e.g., propylene carbonate and propylene oxide, are preferably separated from the reaction mixture. Concurrently, thallic compounds, e.g., thallic acetate, are reduced to the thallous form e.g. thallous acetate, during the formation of the alkylene carbonates and oxides. These thallous compounds may be reoxidized back to their thallic state for subsequent reuse by contact with molecular oxygen in the presence of a catalyst under suitable reaction conditions.

DETAILED DESCRIPTION OF THE INVENTION

The process of this invention is broadly applicable to a cyclic process for the direct formation of alkylene carbonates and oxides, together with minor amounts of other organic compounds, from the reaction of the corresponding olefin with carbon dioxide and a thallic oxide and a weak acid, or, a weak acid thallic salt in an aqueous organic solvent medium. Alkylene compounds suitable for use herein, include substituted and unsubstituted aliphatic and alicyclic olefinically-unsaturated compounds which may be hydrocarbons, esters, alcohols, ketones, ethers or the like. Preferred compounds are those having from three to thirty carbon atoms. Illustrative compounds are propylene, normal butylene, isobutylene, the pentenes, the methyl pentenes, the normal hexenes, the octenes, the dodecenes, cyclohexene, methyl cyclohexene, butadiene, styrene, vinyl toluene, vinyl-cyclohexene, the phenyl cyclohexenes, and like hydrocarbon olefins. Olefins having halogen, oxygen, sulfur and like substituents can be used. Such substituted olefins are illustrated by allyl alcohol, methallyl alcohol, diallyl ether, methyl methacrylate, methyl oleate, allyl chloride, and the like. Propylene is the preferred species of choice.

While the presence of a thallic (Thallium(III)) compound is essential to the invention, not all thallic compounds are equally useful, most preferred are thallic oxides such as $Tl_2O_3$, in conjunction with weak acids or, more preferably, thallic salts of a weak acid, such as an acetate, propionate, butyrate, or the like which are suitable for use. The preferred thallic compound is thallic acetate. For purposes of this disclosure, the term "weak acid salt" refers to a salt which undergoes reaction conditions while providing a pH of about 2 to 8, and most preferably from about 4 to 7. It has been found that thallic salts of strong acids, such as thallic chloride and thallic nitrate, are substantially less effective. Since thallium is reduced from the thallic to the thallous (Thallium(I)) state during the oxidation reaction the use of thallous compounds is from a cyclic process standpoint, ineffective, unless they can be effectively oxidized back to the thallic state.

Carbon dioxide preferably will be supplied in its liquid state to the reaction zone and preferably is of at least reasonable purity, such as that which is found in commercially available carbon dioxide. Nevertheless, minor amounts of impurities such as carbon monoxide may be tolerated. Inert gases such as nitrogen which do not affect the reaction may also be present in any reasonable amount, so long as the desired carbon dioxide partial pressure is provided. It is preferable that there be a large stoichiometric excess of $CO_2$. The partial pressure of carbon dioxide to be employed in the process of this invention should range between about atmospheric to about 3,000 psia, with the preferred $CO_2$ partial pressure ranging from about 500 to 1,500 psia, and most preferably, between about 800 to 1,200 psia.

The amount of water present in the reaction medium can generally range from about 0.1 to 40 wt. % of the reactants, and preferably is at least 3% and most preferably, from about 5 to 30%. Although the amount of reaction medium can be freely varied, it is preferred that enough be present to dissolve the thallic compounds and to provide a molar ratio of water to thallic compound of at least 1:1, and preferably at least 10:1.

Solvents suitable for use in the process of this invention to form the reaction medium can be selected from a wide variety of water miscible organic solvents. Examples of such solvents are sulfolane, tetrahydrofuran, dioxane, N,N dimethylformamide, dimethylsulfoxide, acetonitrile, methanol, ethanol, propylene glycol, tertiary butyl alcohol, acetone, methyl ethyl ketone, diethyl ketone, and the like, as well as mixtures thereof, with sulfolane as the preferred. The amount of solvent relative to the amount of reactants is not critical, and the reactants may form either a homogeneous mixture or a heterogeneous mixture in the reaction medium. The pH of the reaction medium may vary widely, but it generally ranges from about 3 to less than about 8, and preferably from about 5 to 7. In order to obtain good selectivity of the alkylene carbonate, the pH of the reaction medium should not be below 5. The foregoing pH values are those determined in the aqueous phase.

Although knowledge of the reaction by which olefin, (alkylene) carbonates and oxides are produced from the reaction of the corresponding olefin with carbon dioxide and a thallic compound in an aqueous, miscible organic solvent medium is not essential for a complete understanding of the invention, it may be helpful to set forth the apparent overall stoichiometric reaction, using propylene as the species of choice and thallic acetate as the oxidant:

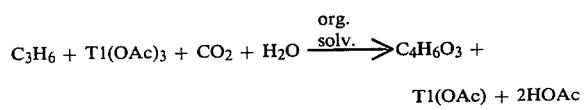

$$C_3H_6 + Tl(OAc)_3 + CO_2 + H_2O \xrightarrow{\text{org. solv.}} C_4H_6O_3 +$$

$$Tl(OAc) + 2HOAc$$

The reaction can be carried out, in theory, at any convenient temperature, e.g., from about room temperature up to the decomposition of thallic compounds which occurs at about 120° C., but for best results, from the standpoint of an acceptable reaction rate, it is advantageous to undertake the reaction at moderate temperatures, e.g., between about 40° to 100° C. and, preferably, about 50° to 80° C. The total pressure to be used in the process of this reaction can range from atmospheric to about 6,000 psia, and preferably about 800 to 1,500 psia.

The reaction can be carried out in any reaction vessel or vessels into which the olefin, carbon dioxide, thallic compound, organic solvent and water can be charged, and which will withstand the reaction operating pressures and temperatures. The reaction vessel should be provided with a suitable inlet for leading the olefin, such as propylene, from its source into the liquid reaction mixture, or, in the alternative, the reaction mixture can be pressured with the olefin up to a desired predetermined temperature and pressure before introduction into the reaction vessel. The reaction can be carried out either batchwise or it can be run continuously. The olefin can either be used in its pure state, or, it can be diluted with an inert gas, e.g., nitrogen, argon, helium or the like if so desired. The presence of a dilutant will, of course, make it necessary to employ a higher pressure to charge the equivalent propylene or other olefin pressure. It is generally advantageous to insure good contact between the reaction ingredients in the liquid reaction mixture, and for this purpose efficient agitation such as a mechanical stirrer or an inert gas is suitably provided. In the most preferred embodiment of the invention, it is preferred to use a two-stage reactor for the process of the invention. It is envisioned that the first stage reactor will primarily undertake the oxidation of the olefin to the corresponding alkylene carbonate and oxide while concurrently reducing the thallic compound, e.g., thallic acetate, to the thallous state. The second stage of the reactor should preferably be used for the back oxidation of the formed thallous compounds, e.g., thallous carboxylates, back to their thallic state. It is most preferred that the reaction products of the olefin oxidation be extracted after the first stage reactor and thereafter separated into the desired product or products. Alternatively, the product alkylene carbonate and oxide can be recovered from the reaction mixture by other conventional extraction techniques, e.g., by distillation and the like.

Back oxidation of the thallous compounds to their thallic state, together with potential subsequent recycling for other usages are well known techniques, which already have been outlined in a variety of publications well known to those in the art. See for example, the references cited in U.S. Pat. No. 4,192,814.

The following examples are provided to illustrate the invention in accordance with the principles of this invention but are not construed as limiting the invention in any way except as indicated by the appended claims.

EXAMPLE 1

3.6 g of thallic acetate sesquihydrate (8.8 mmole), 30 g sulfolane and 6.0 g of water were added to a 300 cc. stainless steel Autoclave Engineers Magnedrive Autoclave. The autoclave was cooled to −78° C. and 20 g of propylene (0.5 mole) and 127 g carbon dioxide (2.9 moles) were introduced therein. The autoclave was then heated to 50° C. for 2.0 hours, creating a total system pressure of 1,400 psig. The autoclave volatiles were then vented into a methyl ethyl ketone scrubber, followed by treatment in a 0.10 M magnesium chloride-hydrochloric acid scrubber. The first scrubber trapped the volatile oxidized propylene products while the second trapped the remaining propylene oxide which escaped the first trap. The excess hydrochloric acid scrubber was titrated with 0.10 M sodium hydroxide. The organics which remained in the aqueous sulfolane solution were measured by standard gas chromatographic techniques. The analysis detected 0.9 mmoles propylene carbonate (21% yield), 1.8 mmoles propylene oxide, (43% yield) and 0.3 mmoles acetone (7% yield). No propylene glycol monoacetate was detected. 4.2 mmoles of thallous acetate (48% conversion) was detected at pH=6.0.

The yields of oxidized propylene products in this and all the following examples are based on the amount of thallic compound reduced to the thallous state. The conversions of thallic compounds reduced to the thallous state are based on the starting quantity of thallic compound.

EXAMPLE 2

This example shows the effect of varying the carbon dioxide pressure.

3.6 g of thallic acetate sesquihydrate (8.8 mmole), 30 g of sulfolane, 6.0 g of water and 40 g of propylene (1 mole) were added to the same autoclave used in Example 1. The reactor was allowed to reach 0° C., and 750 psi of carbon dioxide was added. The autoclave was heated to 50° C. for 2.0 hours to give a total pressure of 1,100 psig. The analysis detected 1.0 mmoles of propylene carbonate (20% yield), 2.1 mmoles of propylene oxide (44% yield), 0.5 mmoles of acetone (10% yield), and 0.5 mmoles of propylene glycol monoacetate (10% yield). 4.8 mmoles (55% conversion) of thallous acetate was detected at a pH=6.1.

EXAMPLE 3

This example shows the effect of a temperature change in the reaction system.

3.6 g of thallic acetate sesquihydrate (8.8 mmoles), 30 g of sulfolane, 6.0 g of water, 20 g of propylene (0.5 mole), and 106 g of carbon dioxide (2.4 moles) were added to the same autoclave used in Example 1. The autoclave was heated to 80° C. for 2.0 hours to reach a pressure of 1,800 psig. The analysis detected 1.0 mmole of propylene carbonate (16% yield), 1.1 mmoles of propylene oxide (18% yield), 0.3 mmoles of acetone (5% yield), and 0.4 mmoles of propylene glycol monoacetate (6% yield). 6.2 mmoles of thallous acetate (70% conversion) was detected at pH=6.4.

EXAMPLE 4

This example shows the effect of increased water and acetic acid on the system.

3.6 g of thallic acetate sesquihydrate (8.8 mmoles), 30 g of sulfolane, 9.0 g of water, 1.0 g of acetic acid, 40 g of propylene (1.0 moles), and 102 g of carbon dioxide (2.3 moles) were added to the autoclave used in Example 1. The autoclave was heated to 50° C. for 2.0 hours. The analysis detected 1.2 mmoles of propylene carbonate (17% yield), 3.0 mmoles of propylene oxide (43% yield), 0.7 mmoles of acetone (10% yield) and 0.6 mmoles of propylene glycol monoacetate (9% yield). 7.0 mmoles of thallous acetate (80% conversion) was detected at pH=5.6.

EXAMPLE 5

This example shows the effect of still more added acetic acid.

3.6 g of thallic acetate sesquihydrate (8.8 mmoles), 30 g of sulfolane, 6.0 g of water, 3.0 g of acetic acid (50 mmoles), 20 g of propylene (0.5 moles), and 113 g of carbon dioxide (2.6 moles) were added to the autoclave of Example 1. The autoclave was again heated to 50° C. for 2.0 hours. The analysis detected 3.5 mmoles of propylene oxide (65% yield), 0.9 mmoles of acetone (17% yield), and 0.6 mmoles of propylene glycol monoacetate (11% yield). No propylene carbonate was detected. 5.4 mmoles of thallous acetate (61% conversion) was detected at a pH=6.0.

EXAMPLE 6

This example shows the effect of using a tetrahydrofuran solvent.

3.6 g of thallic acetate sesquihydrate (8.8 mmoles), 30 g of tetrahydrofuran, 9.0 g of water, 1.0 g of acetic acid (17 mmoles), 40 g of propylene (1.0 moles), and 103 g of carbon dioxide (2.3 moles) were added to the autoclave used in Example 1. The autoclave was again heated to 50° C. for 2.0 hours. The analysis detected 1.0 mmoles of propylene carbonate (15% yield), 3.4 mmoles of propylene oxide (52% yield), 1.5 mmoles of acetone (23% yield), and 0.4 mmoles of propylene glycol monoacetate (6% yield). 6.6 mmoles of thallous acetate (77% conversion) was detected in solution at pH=5.9.

EXAMPLE 7

This example shows the effect of no carbon dioxide in the reaction system.

3.6 g of thallic acetate sesquihydrate (8.8 mmoles), 30 g of sulfolane, 3.0 g of water, and 20 g of propylene were added to the autoclave used in Example 1. No carbon dioxide was added. The autoclave was then heated to 50° C. for 2.0 hours. The analysis detected 2.6 mmoles of propylene oxide (47% yield), 0.5 mmoles of acetone (9% yield), and 0.5 mmoles propylene glycol monoacetate (9% yield). 5.5 mmoles of thallous acetate (64% conversion) was detected at pH=6.0. No propylene carbonate was detected.

I claim:

1. A process for the preparation of alkylene carbonates, from a halogen-free reaction, comprising:
   reacting the corresponding olefins with a thallic oxide and a weak acid or, a weak acid thallic salt, together with carbon dioxide in an aqueous, organic solvent medium;
   separating the formed alkylene carbonates from the reaction medium.

2. A process as claimed in claim 1 wherein the olefin is propylene.

3. A process as claimed in claim 1 wherein the reaction is carried out at pressures ranging from about atmospheric to 6,000 psia and temperatures ranging from about 40° to 100° C.

4. A process as claimed in claim 3 wherein the pressure ranges from about 800 to 1,500 psia and the temperature ranges from about 50° to 80° C.

5. A process as claimed in claim 1 wherein the molar ratio of thallic oxide or thallic salt to water ranges from 1:1 to 1:10.

6. A process as claimed in claim 1 wherein the $CO_2$ partial pressure ranges from about 500 to 1,500 psia.

7. A process as claimed in claim 1 wherein the process is carried out at a pH in the range of 3 to 8.

8. A process as claimed in claim 1 wherein the organic solvent is sulfolane.

9. The process of claim 1 wherein the thallic salt of a weak acid is selected from the group consisting of acetate, propionate and butyrate.

10. A process as claimed in claim 1, further comprising the step of back oxidizing the thallous compounds reduced during the preparation of the alkylene carbonates with molecular oxygen and an effective catalyst and reusing the reoxidized thallic compounds.

11. A process as claimed in claim 10 wherein the reoxidized thallic compound is thallic acetate.

12. A process as claimed in claim 1 wherein the amount of water in the reaction medium can range from about 0.1 to 40 wt % of the reactants.

* * * * *